(12) United States Patent
Maeda et al.

(10) Patent No.: US 6,819,416 B2
(45) Date of Patent: Nov. 16, 2004

(54) DEFECT INSPECTION METHOD AND APPARATUS THEREFOR

(75) Inventors: Shunji Maeda, Yokohama (JP); Atsushi Yoshida, Toyohashi (JP); Yukihiro Shibata, Fujisawa (JP); Minoru Yoshida, Yokohama (JP); Sachio Uto, Yokohama (JP); Hiroaki Shishido, Yokohama (JP); Toshihiko Nakata, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/295,909

(22) Filed: Nov. 18, 2002

(65) Prior Publication Data

US 2003/0095251 A1 May 22, 2003

Related U.S. Application Data

(63) Continuation of application No. 09/797,597, filed on Mar. 5, 2001, now Pat. No. 6,556,290.

(30) Foreign Application Priority Data

Jul. 27, 2000 (JP) ........................................ 2000-231382

(51) Int. Cl.$^7$ .............................................. G01N 21/00
(52) U.S. Cl. ............................... 356/237.2; 356/237.1; 356/237.5; 250/559.42
(58) Field of Search .......................... 356/237.1–237.6, 356/600–601, 614, 364–369; 250/586, 559.41, 559.42, 559.44; 382/141

(56) References Cited

U.S. PATENT DOCUMENTS

| | | | |
|---|---|---|---|
| 4,619,508 A | 10/1986 | Shibuya et al. ............. | 353/122 |
| 4,791,586 A | 12/1988 | Maeda et al. | |
| 4,930,896 A | 6/1990 | Horikawa ..................... | 356/609 |
| 4,974,919 A | 12/1990 | Muraki et al. .............. | 359/204 |
| 5,331,169 A | 7/1994 | Tanaka et al. ........... | 356/237.7 |
| 5,333,052 A * | 7/1994 | Finarov ....................... | 356/369 |
| 5,430,548 A | 7/1995 | Hiroi et al. .................. | 356/394 |
| 5,479,252 A | 12/1995 | Worster et al. .......... | 356/237.5 |
| 5,649,022 A * | 7/1997 | Maeda et al. ................ | 382/141 |
| 5,717,518 A | 2/1998 | Shafer et al. ............... | 359/357 |
| 5,764,363 A | 6/1998 | Ooki et al. .................. | 356/364 |
| 6,091,075 A * | 7/2000 | Shibata et al. ......... | 250/559.44 |
| 6,326,636 B1 | 12/2001 | Isoda et al. ................. | 250/586 |

FOREIGN PATENT DOCUMENTS

| | | |
|---|---|---|
| JP | 61-212708 | 6/1986 |
| JP | 7-318326 | 12/1995 |
| JP | 8-320294 | 12/1996 |
| JP | 2000-193443 | 7/2000 |

* cited by examiner

Primary Examiner—Frank G. Font
Assistant Examiner—Sang H. Nguyen
(74) Attorney, Agent, or Firm—Antonelli, Terry, Stout & Kraus, LLP

(57) ABSTRACT

A method of inspecting a pattern formed on a substrate, comprising the steps of emitting an ultraviolet laser beam from a light source, polarizing the ultraviolet laser beam, scanning the polarized ultraviolet laser beam on a pupil of an objective lens, illuminating a sample with the polarized ultraviolet laser beam after the polarized ultraviolet light beam has passed through the objective lens, analyzing light reflected from the sample as a result of the illuminating step after the reflected light has passed through the objective lens, detecting an image of the sample formed by the analyzed light with a time delay integration sensor, outputting signals corresponding to the detected image of the sample from the time delay integration sensor in parallel, and processing the parallel signals outputted from the time delay integration sensor to detect a defect of a pattern on the sample.

22 Claims, 19 Drawing Sheets

AS　　　　　　　　　　FS

AS FS

FIG. 6A
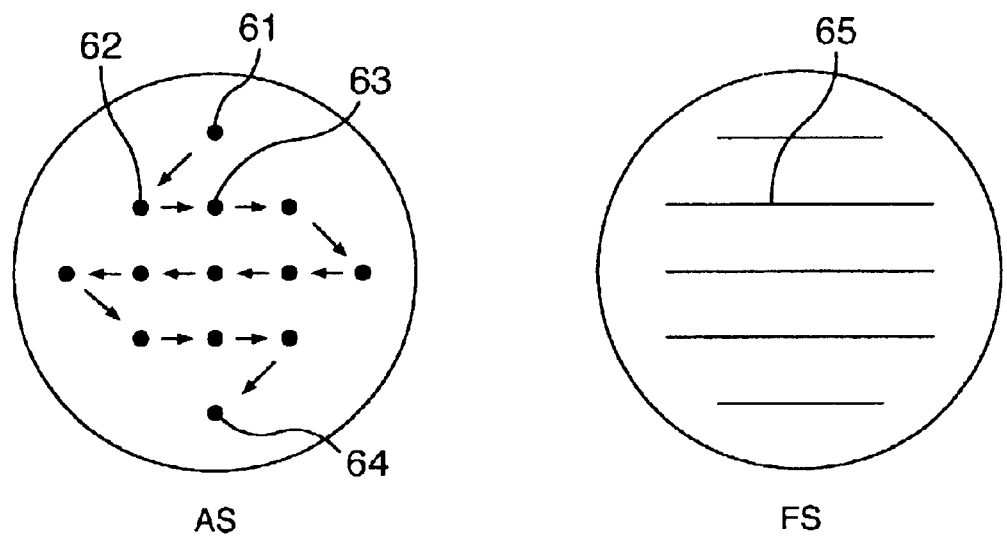
AS  FS
FIG. 6B  FIG. 6C
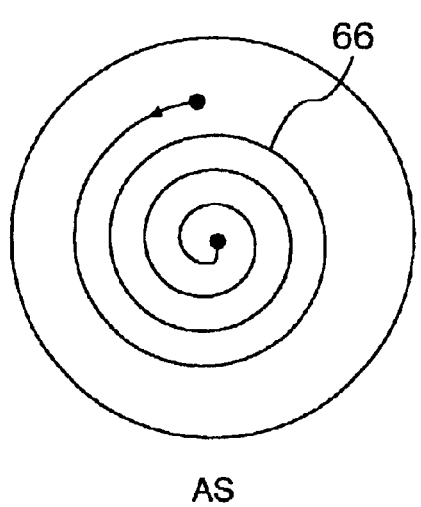 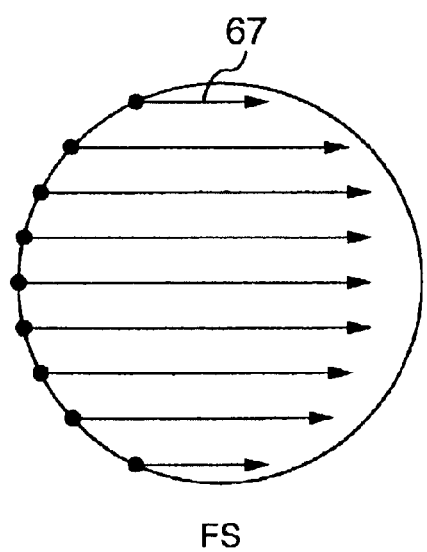
AS  FS

FS a)

b)

FIG. 26
a)
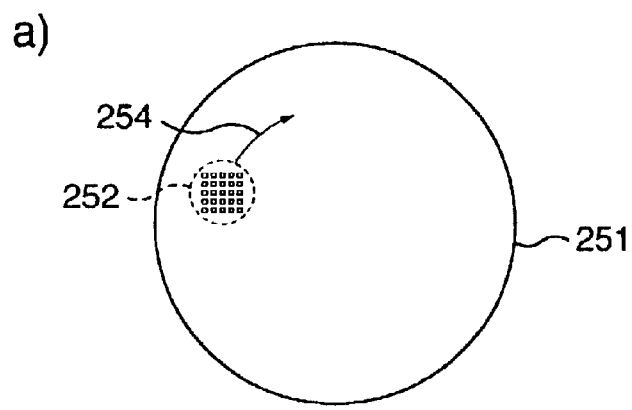
b)
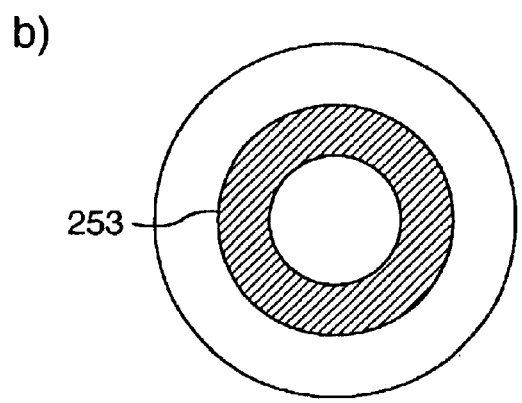
FIG. 27
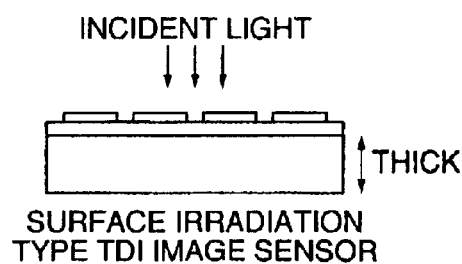
SURFACE IRRADIATION
TYPE TDI IMAGE SENSOR
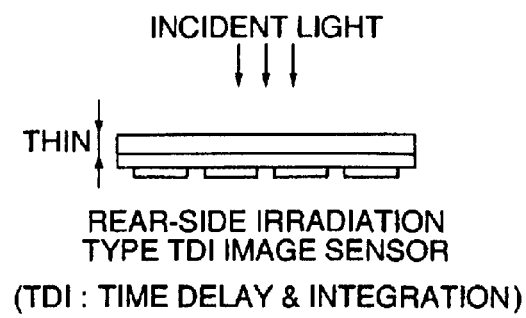
REAR-SIDE IRRADIATION
TYPE TDI IMAGE SENSOR
(TDI : TIME DELAY & INTEGRATION)

DEFECT INSPECTION METHOD AND APPARATUS THEREFOR

CROSS-REFERENCE TO RELATED APPLICATION

This application is a continuation of application Ser. No. 09/797,597 filed on Mar. 5, 2001, now U.S. Pat No. 6,556,290 the contents of which are hereby incorporated herein by reference in their entirety.

BACKGROUND OF THE INVENTION

The present invention generally relates to pattern inspection and foreign substance inspection technology for detecting defects (such as short circuit and disconnection) and foreign objects on a pattern being examined, and particularly to a defect inspection method for examining defects and foreign objects on a pattern such as semiconductor wafer, liquid crystal display and photomask, and to a defect inspection apparatus using that method. In the following description, it is assumed that the defect includes a foreign object.

There is known an inspection apparatus of this kind. As disclosed in JP-A-7-318326 (prior art 1), while a pattern to be examined is being moved, an imager such as line sensor is used to detect the image of the pattern, and the detected image signal and an image signal a certain time delayed from that signal are compared in their brightness so that a disagreement therebetween can be recognized as a defect. In addition, another example is disclosed in JP-A-8-320294 (prior art 2).

According to the prior art 2, when a pattern to be inspected is a semiconductor wafer of which the chip areas each have, in a mixed state, high-density pattern regions such as memory mats, and low-density pattern regions such as peripheral circuits, the detected analog pattern image signal is converted to a digital image signal, and further converted to a signal of gradations so that the high-density and low-density regions have a certain brightness or contrast ratio decided from the brightness frequency distribution of the detected image, and this gradation image signal is aligned with and compared with a separate gradation image signal so that fine defects can be examined with high accuracy.

In the recent LSI production, the circuit pattern formed on the wafer has been developed to a very fine pattern such as a line width of 0.25 μm or below in accordance with the needs for higher integration. This pattern width is the resolution limit of the image-forming optical system. Therefore, the image-forming optical system is advancing toward use of high NA (numerical aperture) and ultra-high optical resolution technology.

However, the high NA has reached the physical critical limit. Therefore, the wavelength of light to be used for the detection should be reduced to ultraviolet light (UV light or DUV light) region as an essential approach.

Moreover, since the inspection is required to be fast conducted, the method of scanning on a sample by fine laser beam cannot be used. If the laser beam is spread out up to full field of view in order to illuminate at a time, speckles occur, and overshoot and undershoot called ringing are caused at the edges of the circuit pattern, thus degrading the picture quality.

SUMMARY OF THE INVENTION

The present invention, in order to solve the above problems, is to provide a method and apparatus for fast examining a fine circuit pattern with high resolution to detect defects thereon.

According to the invention, a laser source is used as a light source, and means for suppressing the laser speckle from occurring is provided in the light path so that coherency-reduced light is irradiated on the object surface to examine the object image.

According to the present invention, as the means for suppressing the laser speckle from occurring, means is provided to gather rays of light from the light source at a point or a plurality of points on the pupil of an objective lens and to scan those points on the pupil in timing with the accumulation time of a detector.

Moreover, in order to improve the pattern contrast, considering that the polarized state of laser can be freely controlled, the orientation of the polarization of illuminating light and ellipticity are controlled so that the polarized component as part of detected light can be detected.

In addition, a plurality of laser beams are used as light sources, because it is possible to expect not only the increase of the defect detection sensitivity, but also other various effects such as long life and countermeasure against breakdown. Also, laser beams of different wavelengths are used and combined because they are effective for controlling the polarized state. Since each laser output can also be reduced, the life of the laser sources can be extended. The addition of laser beams is made by use of a polarization beam splitter, dichroic mirror or half mirror.

The beams of the same wavelength can be processed, by a polarization beam splitter, to be laser beams of which the polarization directions are perpendicular to each other. The dichroic mirror is able to change the polarization directions of laser beams of different wavelengths to parallel or orthogonal directions. As compared with the half mirror, those processes can be achieved with high efficiency. In addition, the polarized state of one or both of different-wavelength beams can be changed by use of a wave plate.

According to the invention, a laser source for ultraviolet (UV) laser beam is used. Here, UV light and DUV are generally called UV light.

These and other objects, features and advantages of the invention will be apparent from the following more particular description of preferred embodiments of the invention, as illustrated in the accompanying drawings.

BRIEF DESCRIPTION OF THE DRAWINGS

FIGS. 6A through 6C are plan views showing the situations in which the pupil of the objective lens and the filed of view are illuminated by laser illumination according to the invention.

FIG. 26 is plan views to which reference is made in explaining the situations in which the pupil is illuminated by a bracelet-like illumination according to the invention.

FIG. 27 is front views of the TDI image sensor according to the invention.

DESCRIPTION OF THE EMBODIMENTS

Figure 1:
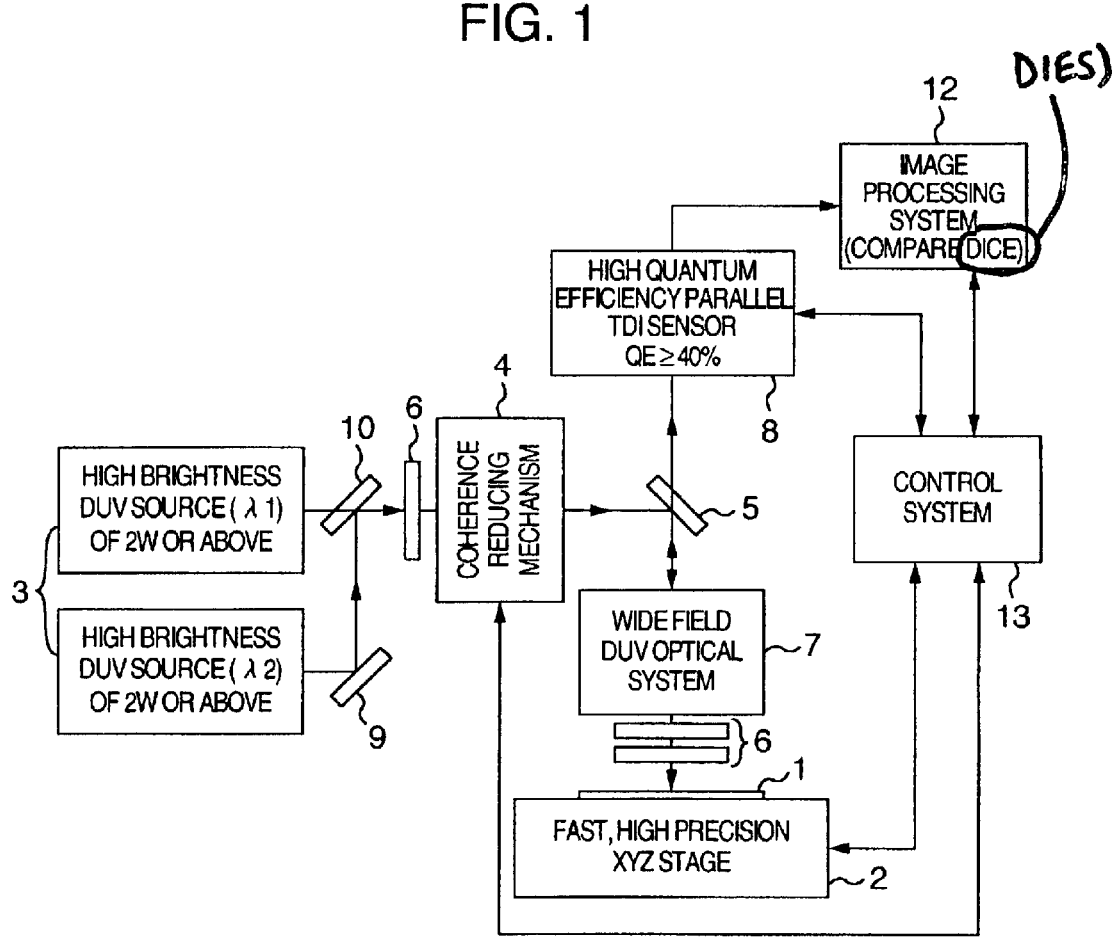
FIG. 1 is a block diagram of the construction of an apparatus for examining a pattern being inspected to detect defects thereon, according to the invention.

Embodiments of the defect inspection method and apparatus according to the invention will be described with reference to the accompanying drawings. FIG. 1 is a diagram showing one embodiment of the apparatus according to the invention. Referring to FIG. 1, there is shown an X, Y, Z, θ (rotation) stage 2 on which a semiconductor wafer 1 is placed as one example of the pattern being examined. There are also shown an optical system 7 including the objective lens, and illumination light source 3 (for example, UV laser sources of 266-nm wavelength and 257-nm wavelength) for illuminating the semiconductor waver 1. Here, while two laser sources are shown, a plurality of laser sources may be provided. In addition, the two wavelengths may be different or equal. These laser sources, when combined, generate various different effects. However, the optical system is corrected for wavelength according to the wavelength.

There is also shown a beam splitter (in some case, it may be a polarization beam splitter or half mirror) 5 that reflects the illumination light from the light source 3 into the optical system 7 so that, for example, bright field illumination is performed on the semiconductor wafer 1 through the optical system. Shown at 6 is a wave plate that is formed of a ½ wave plate and ¼ wave plate. There are shown a coherent reducing mechanism 4 which is, for example, a scanning mechanism for scanning the pupil of the objective lens 7 by the laser beam from the laser source, and an image sensor 8 which generates a shading image signal according to the brightness (shading) of the reflected light from the semiconductor waver 1 as an example of the pattern.

While the semiconductor wafer 1 on the stage 2 is being rotated at an constant speed, and scanned, the image sensor 8 detects the brightness information (shading image signal) of the pattern formed on the semiconductor waver 1.

Shown at 12 is an image processing system which compares the dies and the repeated patterns within a die. Here, the detected image is compared with an image delayed by an amount corresponding to the cell pitch produced from a delay memory 11. The coordinates of the array data on the semiconductor wafer 1 are previously entered through input device (not shown) of keyboard or disk, and a control system 13 generates defect-examined data and forces it to be stored in a memory (not shown) according to these coordinates of array data. The defect-examined data, if necessary, can be displayed on displaying device such as a nonitor display and fed to output device.

The detailed construction of the comparator may be that disclosed in JP-A-61-212708. For example, it is formed of an alignment circuit for images, a differential image detector circuit for aligned images, a disagreement detection circuit for converting a differential image to a binary value and a feature extraction circuit for calculating the area, length (projected length) and coordinates from the binary output.

The light source 3 will be described. For high resolution, it is necessary to select short wavelengths. In the UV wavelength region that provides the best effect for high resolution, it is difficult to obtain high illumination intensity. Discharge lamps are excellent as UV light source, and particularly mercury xenon lamp has brighter line spectra in UV region than other discharge tubes.

Figure 2:
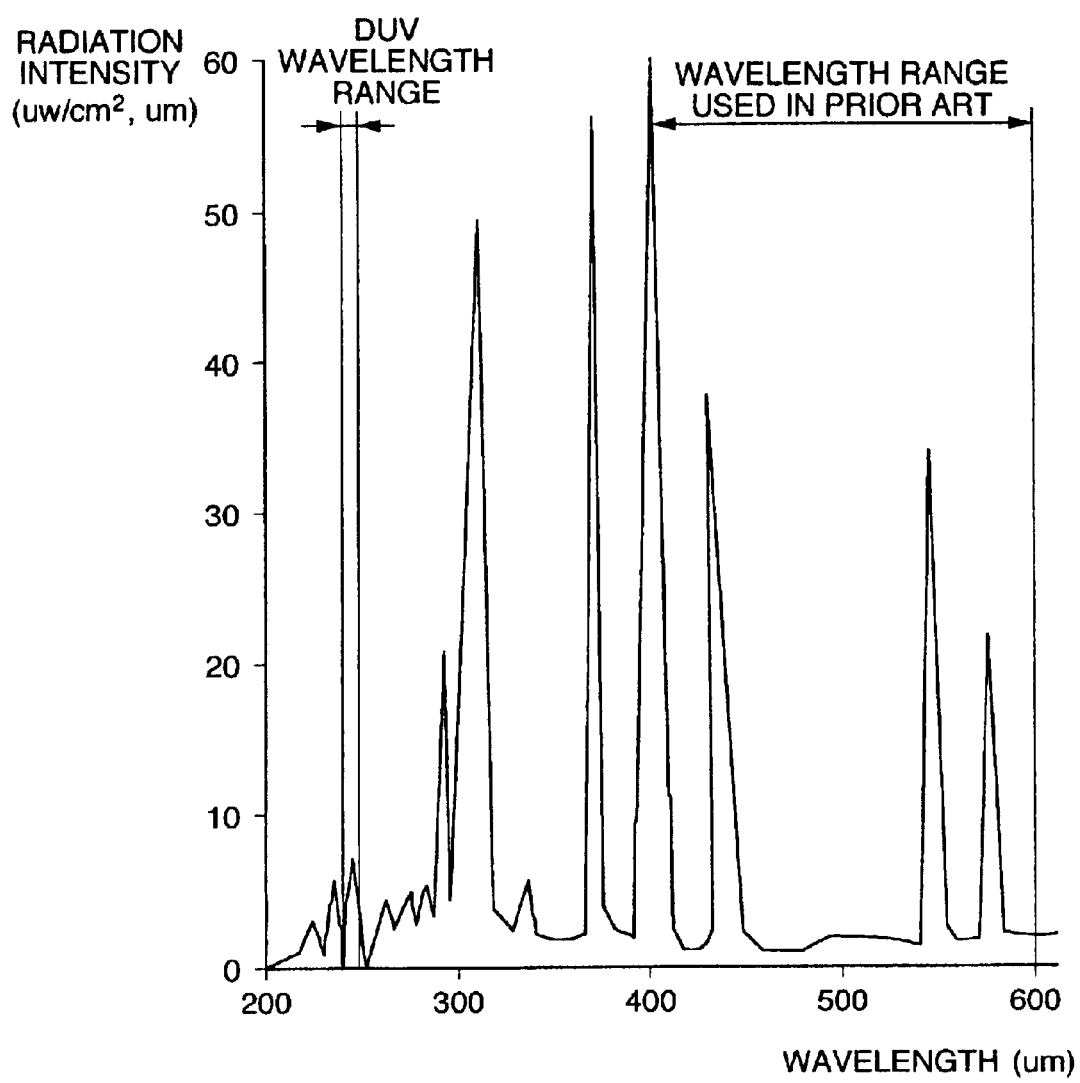
FIG. 2 is a graph showing the emission spectrum of discharge tube illumination.

FIG. 2 shows one example of the radiation intensity of mercury xenon lamp relative to wavelength. The bright line spectra in DUV region are only 1–2% of all output light (the visible light region is about 30%) as compared with the wide visible wavelength range that is used in the prior art). Also, the light radiation is not directional. The efficiency at which the light emitted from the discharge lamp can be led up to the sample cannot be increased even in a carefully designed optical system. Thus, the illumination by the discharge lamp for the UV region cannot offer a sufficient amount of light in the use for fast image detection.

Even if a high-power discharge lamp is used for high illumination (brightness) on the sample, only the luminescent spot size is larger than when a small-power one is used, and thus the brightness (light power per unit area) cannot be increased. Therefore, the laser source is suited for high brightness UV illumination.

Thus, the laser for light source has a large merit. The present invention employs this laser illumination.

Figure 3:
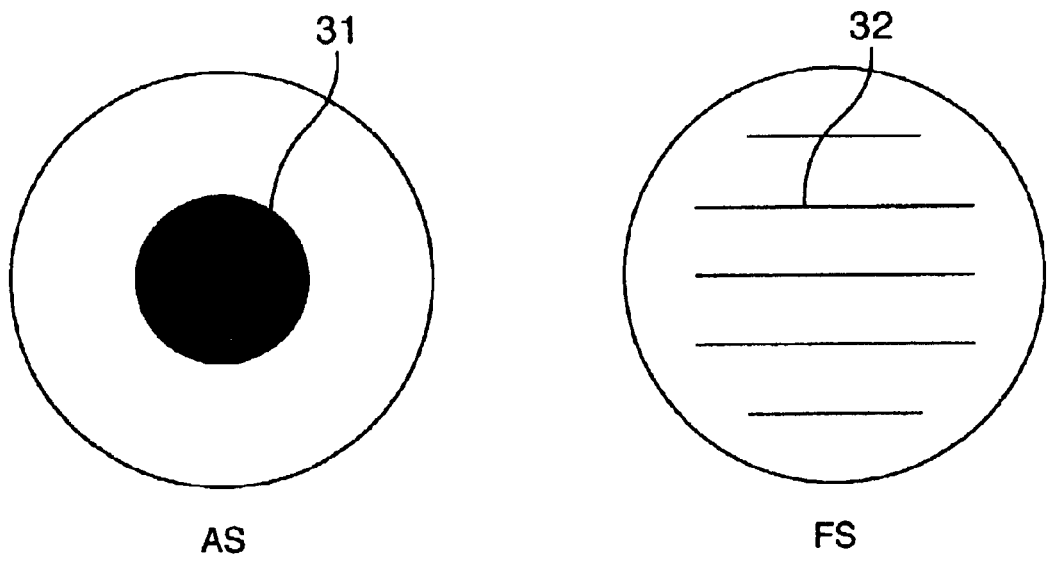
FIG. 3 is a plan view showing the situations in which the pupil of the objective lens and the field of view are illuminated by discharge tube illumination.

FIG. 3 shows the situations in which the objective lens pupil and the field of view are illuminated by normal white light. In FIG. 3, AS indicates the pupil, and FS the field of view. The image of the light source is formed at 31 as a formed image, and the field of view is substantially uniformly illuminated as at 32.

Figure 4A:
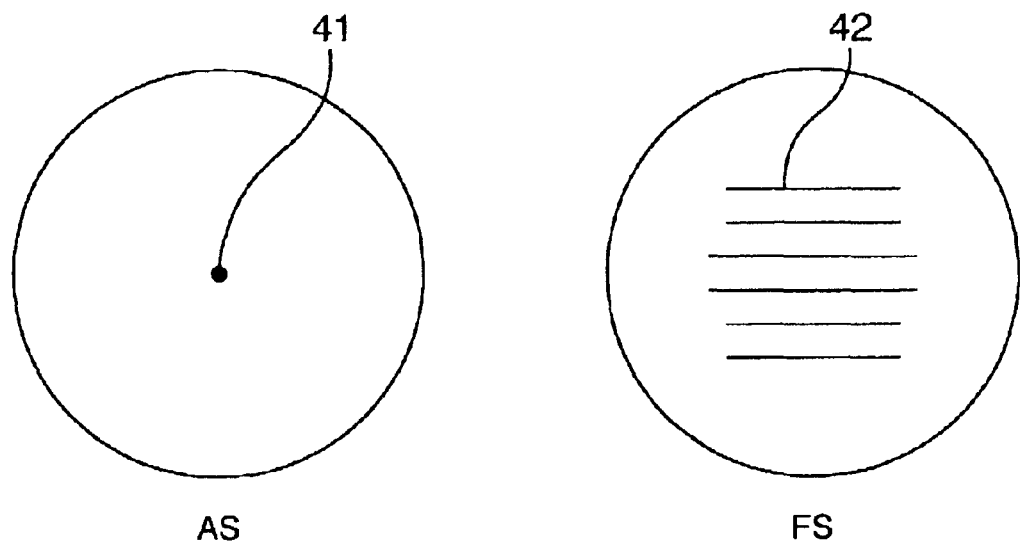
FIG. 4A is a plan view showing the situations in which the pupil of the objective lens and the field of view are illuminated by laser illumination.
Figure 4B:
FIG. 4B is a cross-sectional view of a pattern on the field of view.
Figure 4C:
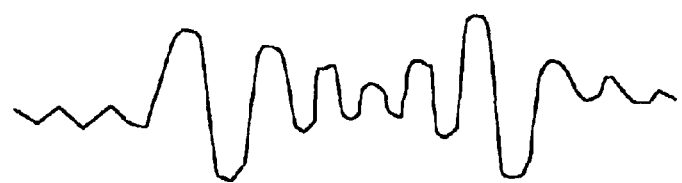
FIG. 4C is a diagram showing a detected signal produced as a result of detecting the pattern (FIG. 4B) on the field of view.

FIG. 4A shows the illumination by a laser source. In this case, the laser source image is formed at a point 41 on the pupil as shown in FIG. 4A. The circuit pattern illuminated as a scan 42 over the field of view, if it is such a cross-sectional pattern as shown in FIG. 4B, is detected to be a waveform as shown in FIG. 4C. When the circuit pattern is illuminated by a laser source and detected to produce the image of the circuit pattern as described above, overshoot and undershoot are caused at the edges of the pattern, and speckle occurs because the σ of the illumination is small. It can be considered that the illumination over the field of view below the objective lens is not performed from various angles relative to the sample. Under the usual white light source, the pupil of the lens is illuminated over a sizable area, and the field of view toward the sample below the lens is illuminated over from a wide angle range equal to the NA (numerical aperture) of the objective lens.

Figure 5:
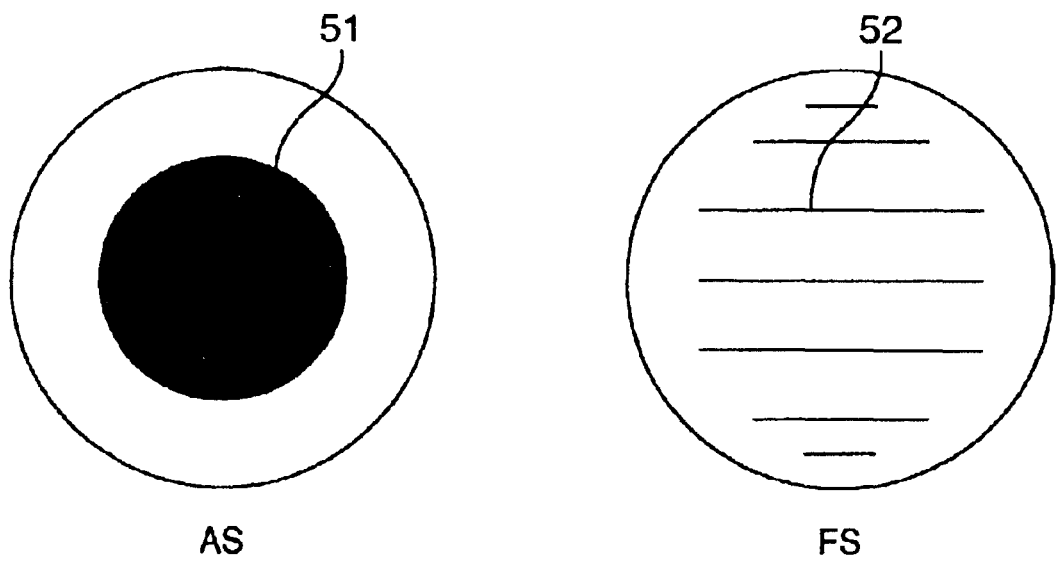
FIG. 5 is a plan view showing the situations in which the pupil of the objective lens and the field of view are illuminated by laser illumination that is spread on the pupil.

The σ of the coherent light such as laser light is 0 (since σ is proportional to the area of light source image on the pupil). Since the coherent light is from a point light source, the image formed on the pupil is a point. Of course, laser light can be spread by another separate lens system to form a light flux 51 on the pupil as shown in FIG. 5. However, since the laser source has coherence, the same thing as when all light rays are irradiated from the position of (σ=0 occurs as a result 52 shown in FIG. 5, and thus the problem cannot be solved yet. Therefore, it is necessary to use the means for reducing the coherence of laser. In order to reduce the coherence, it is necessary to select either time coherence or spatial coherence and reduce.

Thus, according to the invention, the light source image is formed on the pupil of the objective lens of the inspection apparatus, and this image is moved to scan the pupil, for example, first at position 61, next at the position 62, then position 63, . . . so that the field of view can be illuminated over like lines 65 as shown in FIG. 6A. The images of speckle, overshoot and undershoot occur at each position, but have no coherence since they are caused at different times. Thus, when all images as a result of scanning are added on the detector, the same image as the coherent light source can be obtained. A detector of the accumulation type, such as CCD is suited for the addition on the detector.

Figure 19:
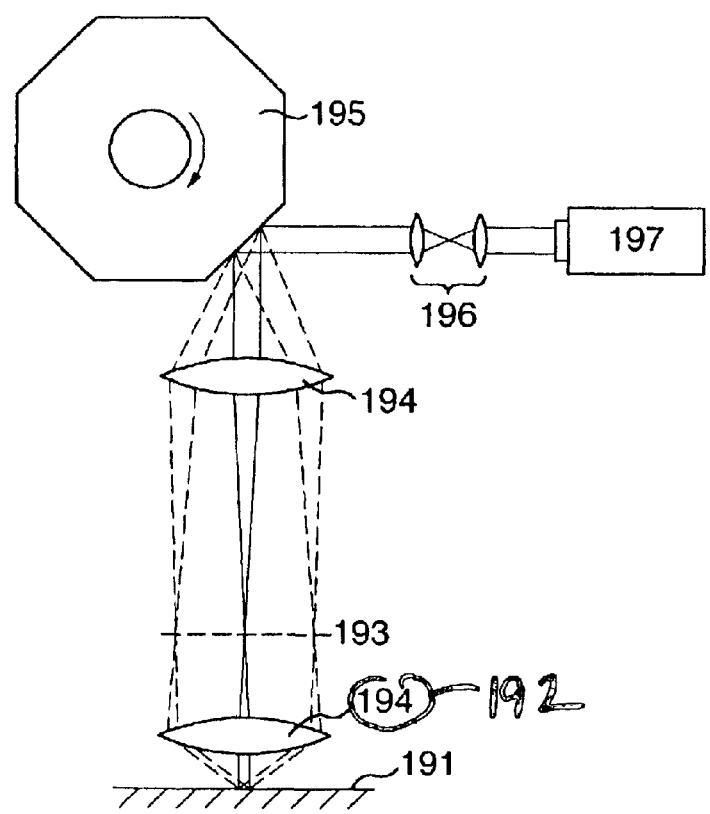
FIG. 19 is a front view of an embodiment of the mechanism for scanning the pupil by the laser illumination according to the invention.

FIG. 19 shows an example of the construction for scanning the laser spot on the pupil of the objective (detection/illumination) lens according to the invention. In this figure, only the illuminating side structure is shown, the detecting side construction being not shown. For the sake of explaining the principle, only the one-dimensional scanning mechanism is shown.

The beam (which is parallel because of laser beam) from a laser source 197 is shaped into a necessary beam shape by a beam shaping mechanism 196, and deflected by a scanning mechanism 195. Here, a polygon mirror is shown as an example of the scanning mechanism. The deflection angle of the deflected parallel beam is converted to the change of position by an f–θ lens 194 called condenser lens. Thus, the lens 194 is placed at a position separated by the focal distance of the lens 194 away from the scanning mirror surface. The beam from the lens 194 is converged on a pupil plane 193 of an object lens 192. Therefore, the distance between the lens 194 and the pupil plane 193 is also equal to the focal distance of the lens 194. Thus, the laser beam from the object lens 192 is, while its direction angle is being changed, irradiated on the sample, 191.

Figure 20:
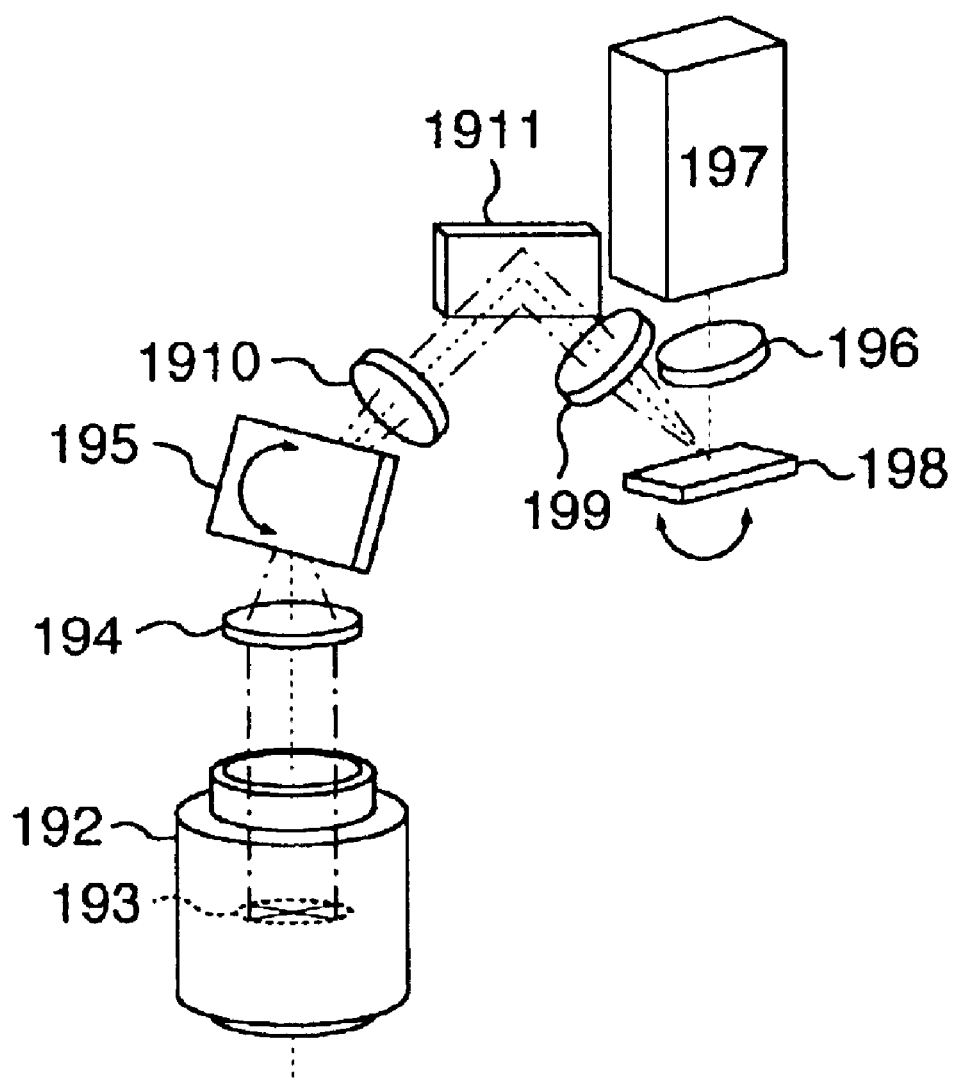
FIG. 20 is a front view of an embodiment of the mechanism for two-dimensionally scanning the pupil by the laser illumination according to the invention.

FIG. 20 shows the case in which the laser beam is deflected to scan the pupil in a two-dimensional manner. In this figure, a plate-like mirror such as a galvano mirror is shown as one example of the scanning mechanism. It may be a movable mirror produced by a micro machine. In addition, a mirror 1911 shown in the figure is used to bend the light path, and thus is not essential. Therefore, this structure is different from the construction shown in FIG. 19 in that an f–θ lens 199, a scanning mirror 198 as the scanning mechanism for one more axis, and an incidence lens 1910 to the scanning mirror 195 are added. The construction shown in FIG. 20 can achieve the two-dimensional scanning shown in FIG. 6.

The NA of the objective lens 192 in this embodiment is 0.75. The larger the NA, the greater the pupil scanning effect, thus reducing the influence of light interference caused by the thin film patterns (since the brightness of pattern depends on its film thickness, so that the difference of a defective portion to the correct portion becomes great in the pattern comparison which will be described later, it is difficult to detect a fine defect. Even if there is a very small thickness change called "grain" or "hillock", the brightness change becomes great).

Figure 21:
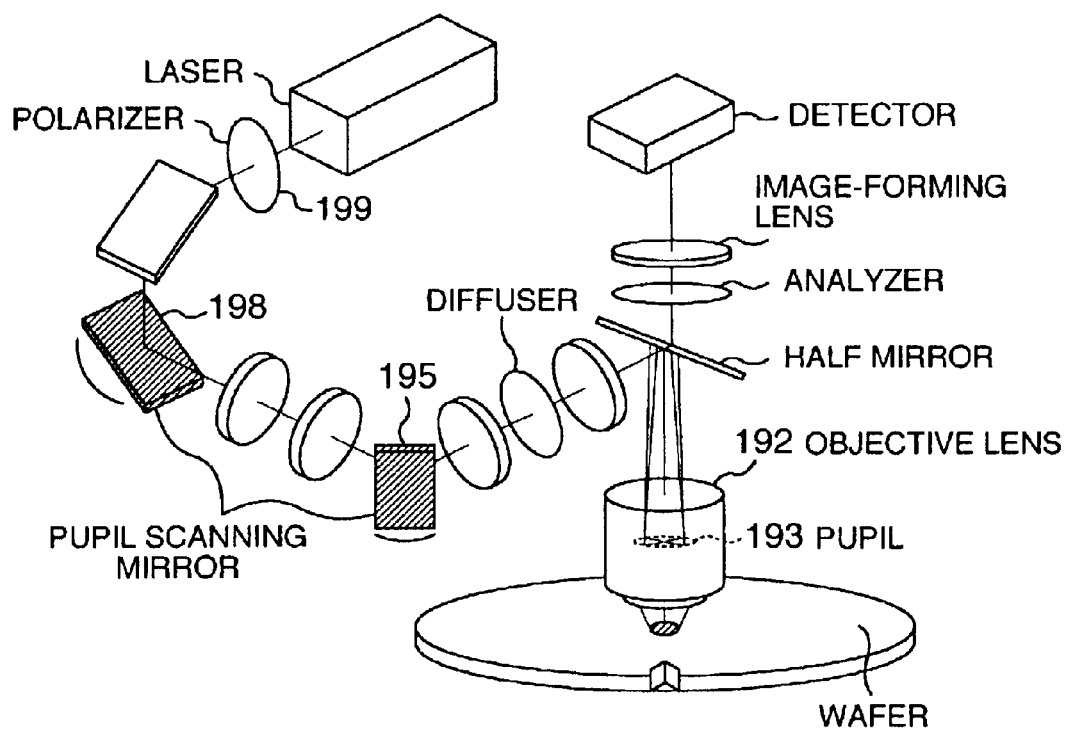
FIG. 21 is a plan view of an embodiment of the mechanism for scanning the pupil by the laser illumination according to the invention, with a diffuser inserted in the light path.

FIG. 21 shows an example of the construction having a diffuser placed in the light path. The diffuser is placed at a conjugate position to the pupil 193 of the object lens 192. In this example, since the laser beam is deflected to scan the diffuser, the coherence reducing effect is greater. Of course, the diffuser may be fast reciprocated or rotated in the direction perpendicular to the optical axis of the laser beam.

Figure 17:
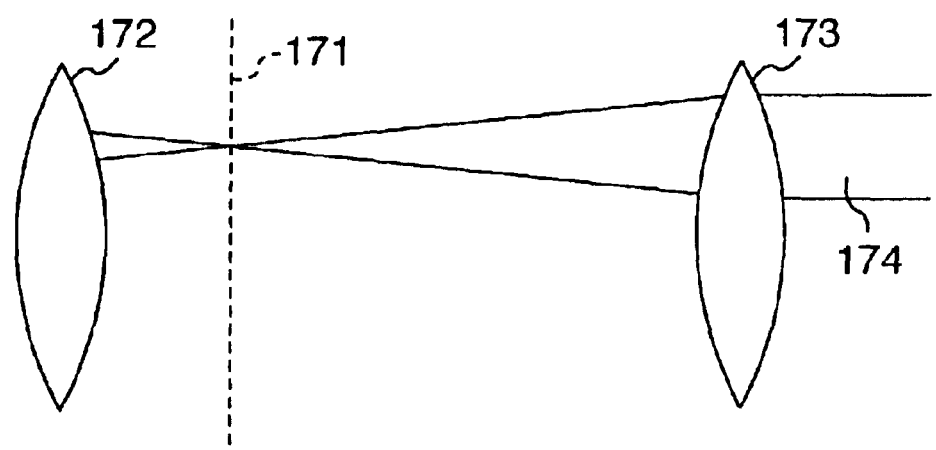
FIG. 17 is a front view of an optical system to which reference is made in explaining the situation in which light of laser illumination according to the invention is converged on the pupil of the objective lens.
Figure 18:
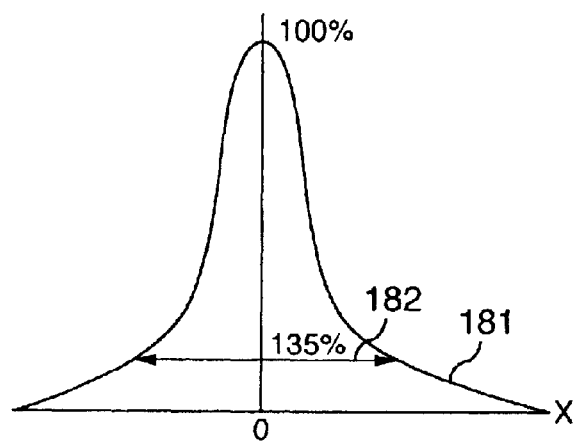
FIG. 18 is a graph showing the intensity distribution of beam from the laser source.

The light source image is formed on the pupil by converging the laser beam from the laser source through a condenser on a pupil plane 171 of an objective lens 172 as shown in FIG. 17 (when image detection is made under the bright field illumination, the illumination or irradiation lens and the detection lens are shared by one lens). Here, the laser beam from the laser source as a point source forms a spot when converged up to the diffraction limit. In other words, all the laser beam output is concentrated to this spot, and thus the power at this spot is considerably large.

The actual objective lens is formed of a large number of lenses (at most ten lenses) in order to compensate for the aberration. Thus, the pupil plane 171 is located at a position not only away from the lens, but also within the lens (glass material portion) or near the lens surface, depending upon the design of the objective lens. In this case, the coating (for reflection prevention) formed on the lens may be damaged when it is exposed to high-power laser beam, thus causing a serious problem. The confocal laser scanning microscope usually called laser scanning microscope makes the laser beam spread on the pupil plane, while the present invention forms the spot on the pupil plane (on the other hand, the laser scanning microscope narrows the spot down on the sample, and thus there is the possibility that the sample is damaged).

In the present invention in which the pupil plays a great role for the objective lens, the pupil plane position is previously set to be separated from the lens surface, thereby avoiding the problem from occurring. When the pupil plane is separated from the lens surface, the spot is out of focus, and hence its diameter is slightly larger with the result that the average power density is lowered.

Moreover, when the pupil plane cannot be separated enough away from the lens surface because of the object lens structure, only that lens can be allowed not to be coated. The inventors think that if only a component of the lens is not coated, the effect of all the object lens on the transmissivity is small, and that the proof strength of the coatings in that case can be kept enough.

In addition, a continuous oscillation type laser should be desirably selected as the laser source. The reason for this is that the pulse oscillation type laser generates a very high power laser pulse output (peak), thus leading to a damage to the lens even though the average output can be restricted to a low value. Of course, a small-output laser free from care about damage may be of the pulse oscillation type.

The laser spot thus formed on the pupil may be moved to scan by spiral scanning 66 or television (raster) scanning 67 as shown in FIGS. 6B and 6C, or by other scanning operations. In this case, however, it is desired to make the unit scanning within the accumulation time of the detector. Therefore, the scanning should be synchronized with the operation of the detector. For example, referring to FIG. 20, when the pupil plane is scanned in a ring shape (such scanning as shown in FIG. 26, which will be described later), the galvano mirrors 195, 198 may be driven with a fundamental period of 1 kHz if the accumulation time of the image sensor is 1 m sec. In addition, the stage, the sensor and the pupil plane scanning should be synchronized with each other. In this case, the stage has the largest inertia, and thus it is most difficult to synchronize.

The pupil plane scanning optical system can easily synchronize over a wide frequency range or a limited frequency range depending upon the type of the mechanism. Moreover, since the sensor is formed of an electric circuit, the synchronization is easy. Thus, if the basic synchronizing signal is generated from the position of the stage, the two other portions can be easily synchronized with the stage. This method is desirable.

Figure 16:
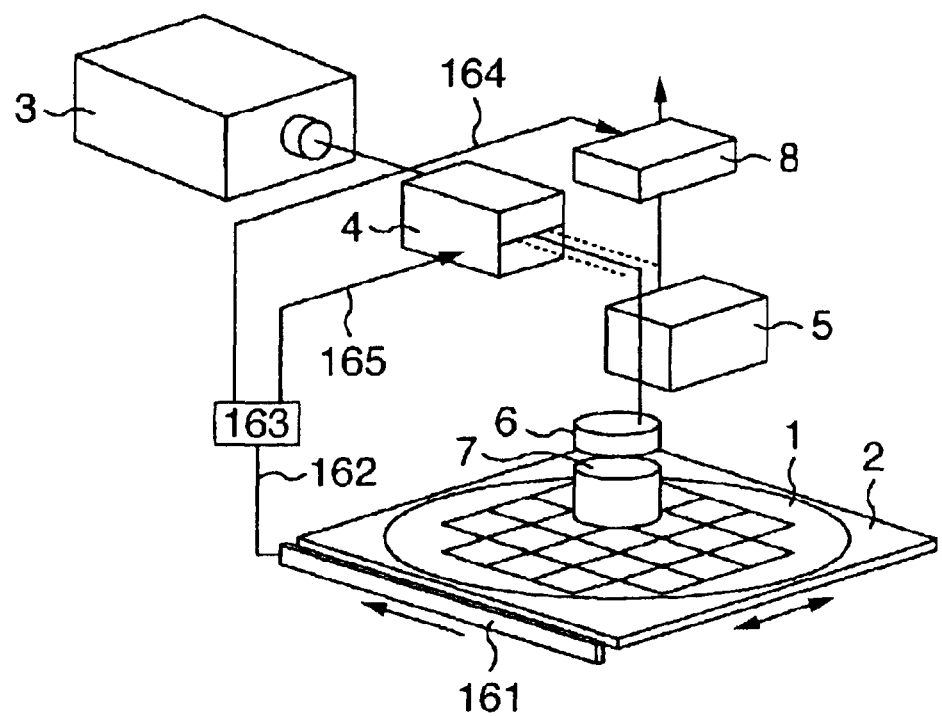
FIG. 16 is a perspective view of the apparatus for examining the pattern to detect defects thereon according to the invention, by synchronizing the stage, pupil scanning optical system and sensor.

FIG. 16 shows that system. The stage position is determined by a position detection mechanism 161 such as a linear encoder mounted on the XY stage 2, and fed to a synchronizing signal generator 163, which then generates a sync signal 164 such as a sensor transfer pulse, and a sync signal 165 for the pupil plane scanning mechanism.

The pupil plane scanning mechanism can be most easily synchronized when an electric signal to the A/O deflector or E/O deflector is converted directly to the deflection angle of light. The deflector may be the type in which a galvano mirror or polygon mirror is used as a basis.

Thus, the image of illumination 65 can be obtained over the field of view as illustrated in FIG. 6A at FS. Here, use of two wavelengths has the effect of reducing the coherence.

The laser beam synthesizer 10 will be described. Two laser beams are synthesized by use of, for example, a polarization beam splitter (PBS). In this case, if the polarization directions are made perpendicular, the synthesis can be made with high efficiency. The two laser wavelengths may be different or equal. A dichroic mirror may be used instead of the polarization beam splitter. In this case, the two laser wavelengths are assumed to be different. The dichroic mirror synthesizes the beams by use of the difference between the wavelengths. In this case, the polarization directions may be equal or parallel. The half mirror may use the beams of different polarization directions, but reduces the efficiency of the synthesis. Also, it can be considered that the ½ wave plate 6 corresponding to the wavelength is placed, and the polarization directions are made equal by use of the difference between the wavelengths. In any case, it is possible to achieve the most suitable construction considering the efficiency and polarization of the illumination.

Figure 7:
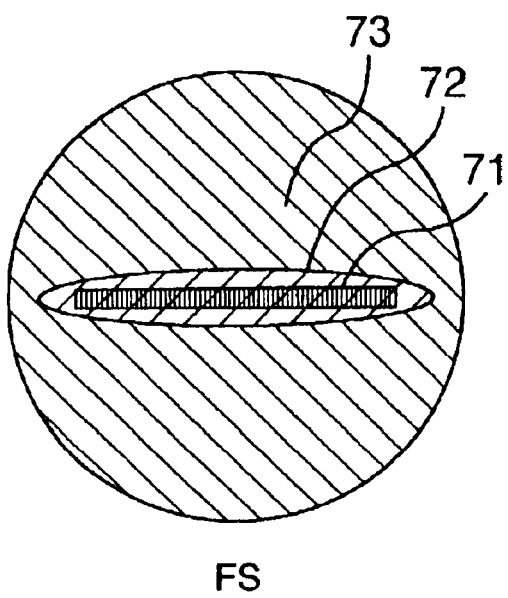
FIG. 7 is a plan view showing the relation between a CCD detector and the illuminated region on the field of view according to the invention.
Figure 8:
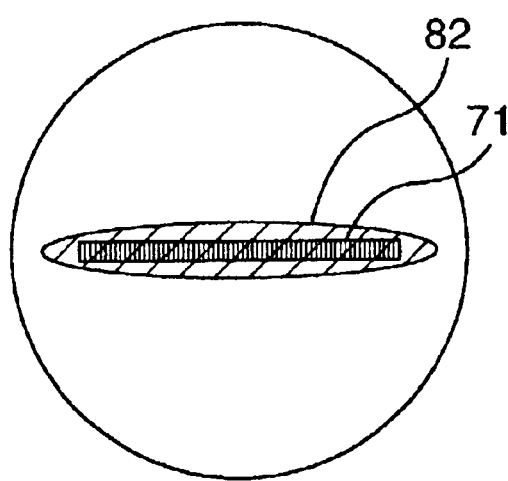
FIG. 8 is a plan view showing the relation between the CCD detector and the illuminated region on the field of view according to the invention.
Figure 9:
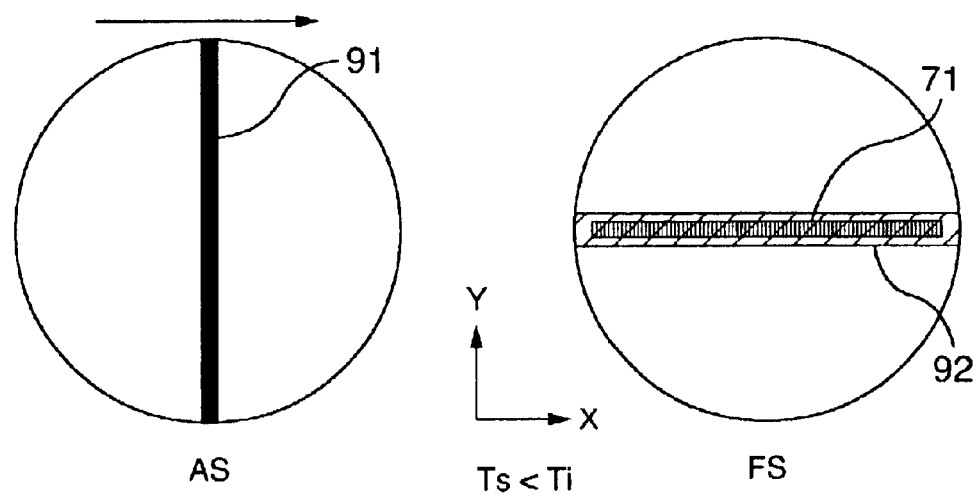
FIG. 9 is plan views showing the CCD detector and the situations in which the pupil of the objective lens and the field of view are illuminated by laser illumination according to the invention.

Let it be considered that a one-dimensional sensor is used as the accumulation type detector. As illustrated in FIG. 7, even if all the field of view is illuminated over against a one-dimensional sensor 71, only a region 72 can contribute to the detection. A region 73 that occupies the most part of the light power does not contribute to the detection. In order to increase the illumination intensity, it is desirable to use linear illumination as indicated by a region 82 against the one-dimensional sensor 71 as shown in FIG. 8. (The CCD scans in the Y-direction on the field of view to thereby produce a two-dimensional image.) In that case, when the pupil plane is illuminated in the longitudinal Y-direction as shown in FIG. 9 at 91, the field of view is illuminated over so that the illumination conforms to the shape of the CCD 71 as shown at 92. In addition, the pupil plane is scanned in the X-direction. The period, Ts of the scanning is shorter than the accumulation time, Ti of the CCD. Thus, the images can be added.

The problem is that since the illumination on the pupil is spread out in the Y-direction from the start, the pupil cannot be scanned in the Y-direction. Therefore, it is impossible to reduce the overshoot and undershoot that the CCD causes in the Y-direction on the field of view. On the contrary, if the length of the illumination in the Y-direction on the pupil is tried to reduce in order for the pupil to be scanned in the Y-direction, the width of the illumination in the Y-direction on the field of view will be spread out, thus the illumination intensity being lowered.

Figure 10:
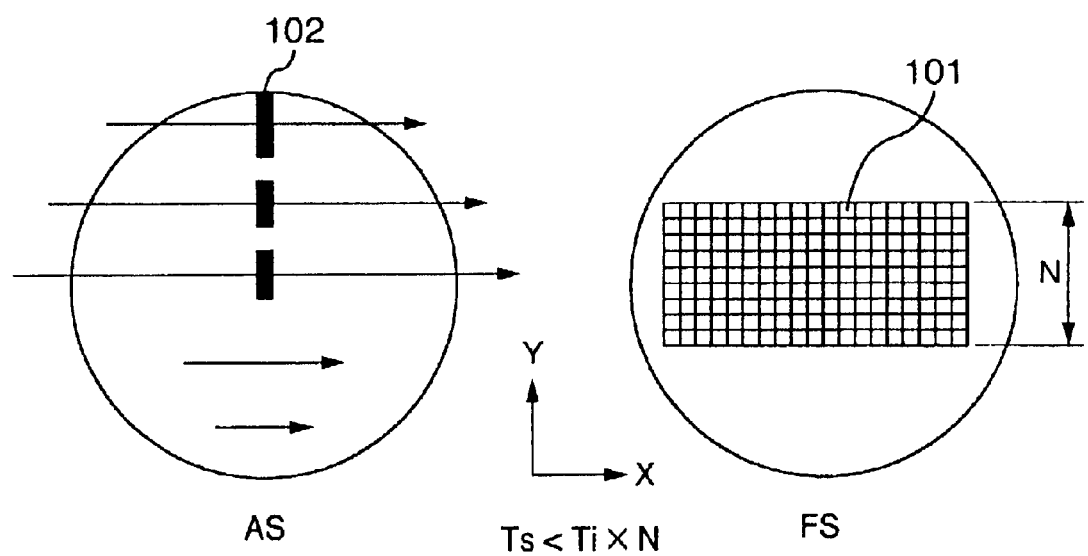
FIG. 10 is plan views showing the TDI detector and the situations in which the pupil of the objective lens and the filed of view are illuminated by laser illumination according to the invention.

According to the invention, this problem can be solved by using a TDI (Time Delay & Integration) type sensor of CCD sensors as shown in FIG. 10. Since the TDI sensor placed on the field of view has N-stage (N is a number of stages such as dozens of stages~about 256 stages.) light-sensitive portions arranged thereon, the illumination light can be detected effectively even if the width of the area illuminated in the field of view is spread N times the normal width.

Therefore, the length of the illumination spot, 102 on the pupil in the Y-direction can be reduced to about 1/N that of CCD, so that the pupil can be scanned in both X-direction and Y-direction. Thus, the overshoot and undershoot that the TDI causes in both X-direction and Y-direction on the field of view can be decreased, and hence the images can be satisfactorily detected. In addition, the period Ts of scanning the pupil is required to be shorter than N times the accumulation time of one stage of the TDI. However, for more uniform detection considering the illumination intensity distribution on the field of view, the scanning period Ts should be selected to be shorter than N/2 times the accumulation time Ti of CCD. In addition, for uniform illumination, the light from the laser source is not converged directly on the pupil, but desirably through a fly eye lens or integrator thereon.

Figure 11:
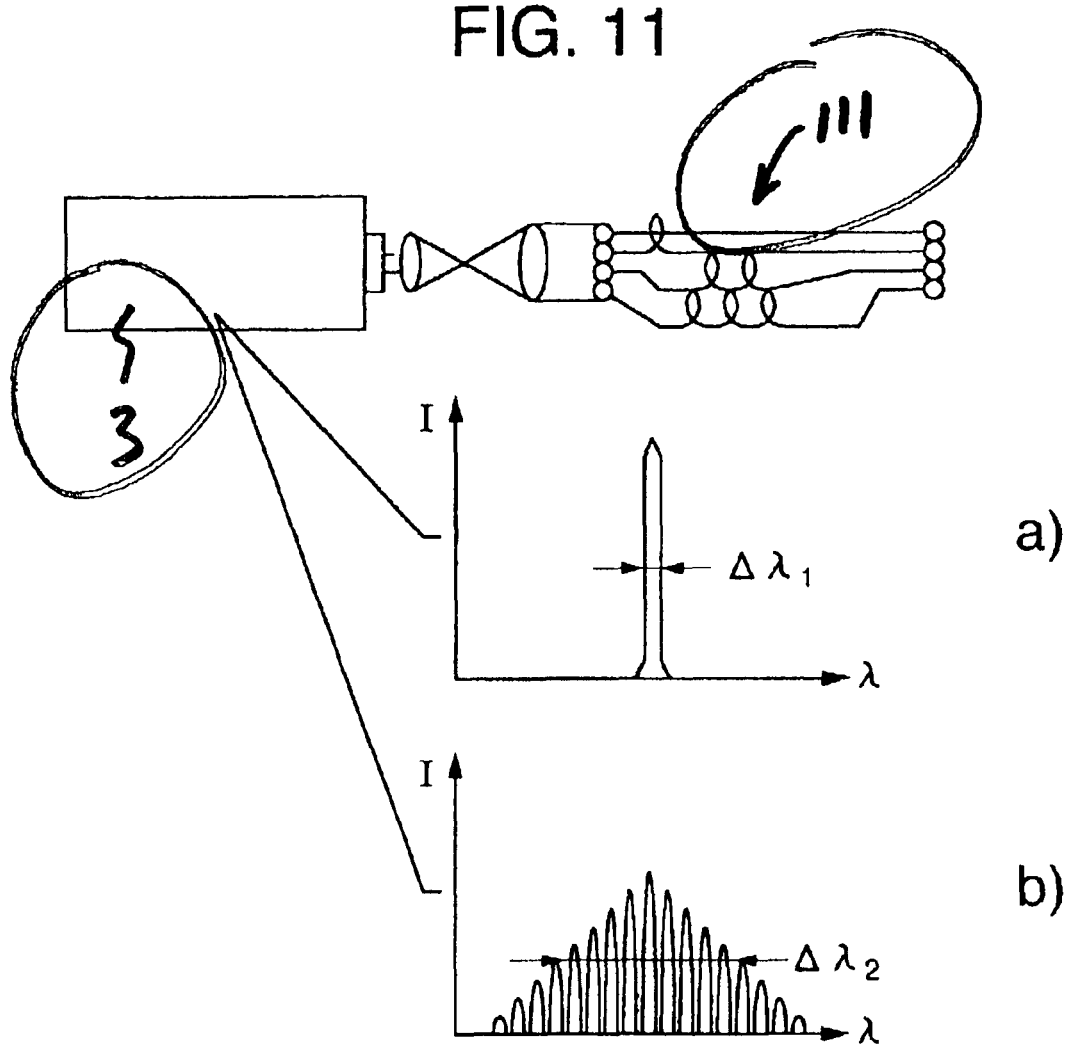
FIG. 11 is a substantially front view of the laser source to which reference is made in explaining a conceptual model for reducing the spatial coherence of laser illumination according to the invention.

A method of reducing the spatial coherence will be described. In order to reduce the spatial coherence, it is necessary to acquire light rays that have a longer light-path difference than the coherence length of laser. More specifically, if the laser beam is incident to a bundle of optical fibers, 111 or glass rods of which the lengths are different as shown in FIG. 11, the output light becomes incoherent (coherent-free). If these fibers are placed on the pupil, the images obtained have no overshoot and undershoot. In this method, the coherence length of laser source should be shorter, and for this purpose the laser source should be selected to oscillate a plurality of longitudinal modes of a wider band $\Delta\lambda_2$ shown in FIG. 11 at b) rather than a single longitudinal mode (oscillation spectrum) of narrow band $\Delta\lambda_1$ in FIG. 11 at a).

Figure 12:
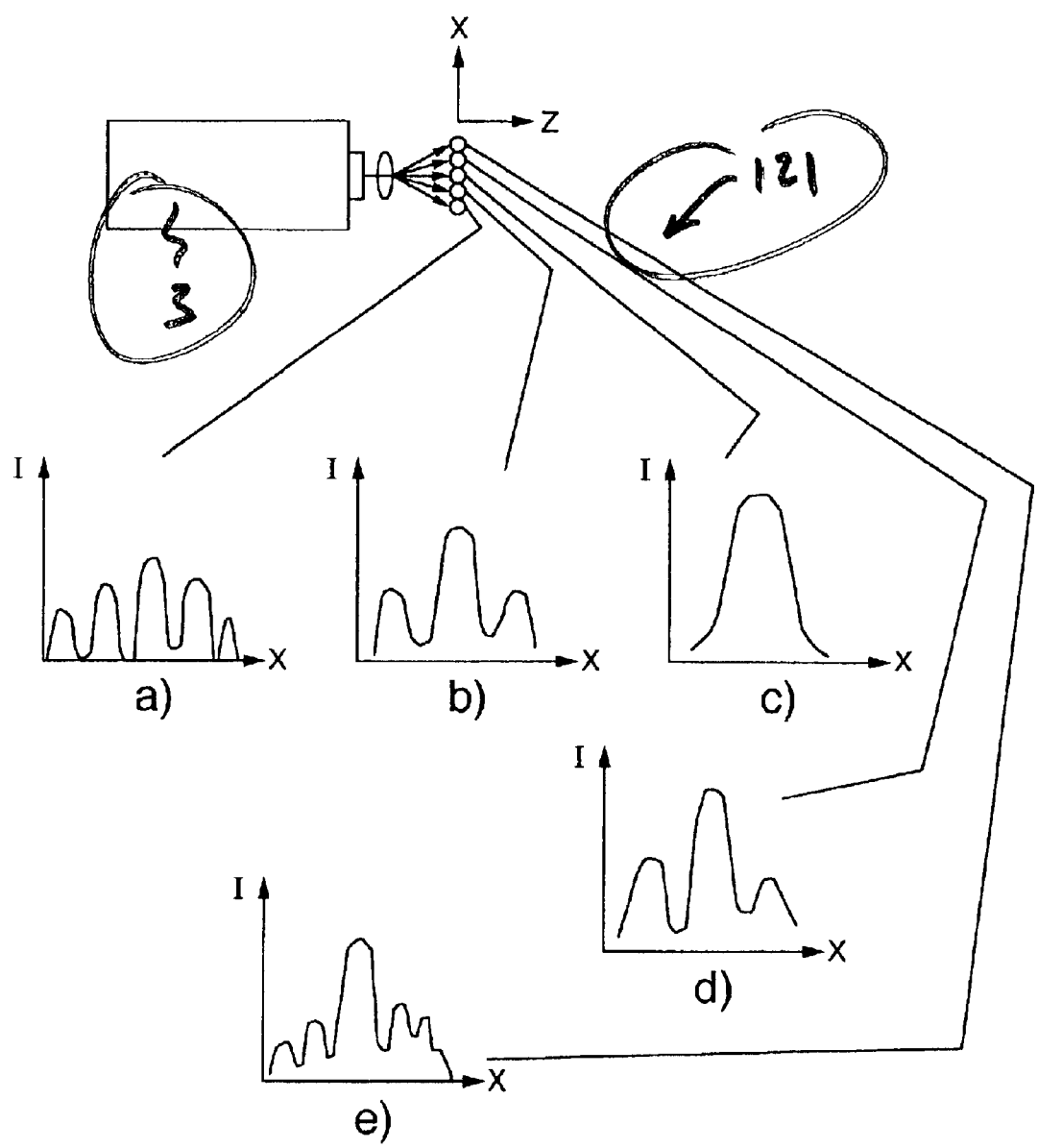
FIG. 12 is a substantially front view of the laser source to which reference is made in explaining a conceptual model for reducing the spatial coherence of laser illumination according to the invention.

Another idea for reducing the spatial coherence employs the phenomenon that when light rays with the optical axis shifted are incident to the optical fibers, the lateral mode (spatial distribution, light intensity I) of the exiting light rays changes. This mode change is usually considered to be unfavorable for industrial applications, and it is a general practice to make efforts toward the reduction of the lateral mode change. The present invention counters this mode change by intentionally shifting the optical axis in various ways and making the light rays incident to fibers 121 so as to produce exiting light rays a), b), c), d), e) . . . with the lateral mode changed differently as shown in FIG. 12. Consequently, the produced exiting light rays are incoherent, and thus irradiated on the pupil. In this method, a very large number of light sources (spots on the pupil) can be produced by bundling a plurality of fibers.

Figure 13:
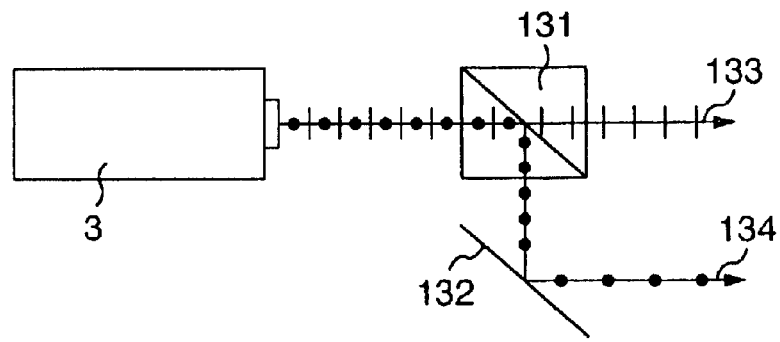
FIG. 13 is a substantially front view of the optical system to which reference is made in explaining a conceptual model for reducing the spatial coherence of laser illumination according to the invention.

FIG. 13 shows the situation in which the beam emitted from the laser source 3 is split by a polarization beam splitter 131 into two laser beams 133, 134 that have polarized planes perpendicular to each other. Shown at 132 is a mirror for changing the direction of the beam. Since the beams having the perpendicular polarized planes have no coherence, light rays with no coherence can be obtained by a very simple construction. In this method, only two light rays can be produced, but rays with no coherence can be obtained with ½ labor hour by combining with the previously mentioned method.

Figure 14:
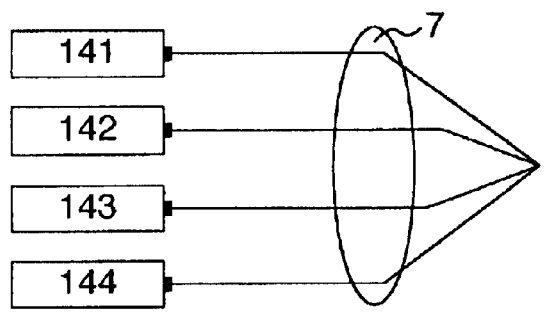
FIG. 14 is a substantially front view of the laser source to which reference is made in explaining a conceptual model for reducing the spatial coherence of laser illumination according to the invention.
Figure 15:
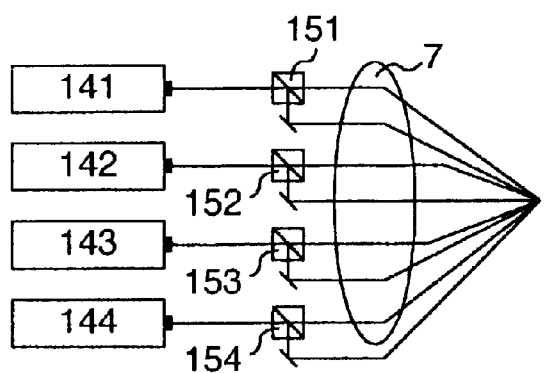
FIG. 15 is a substantially front view of the laser source to which reference is made in explaining a conceptual model for reducing the spatial coherence of laser illumination according to the invention.

In addition, since every light sources independent of each other have no coherence, independent light sources 141, 142, 143, 144 . . . may be used to illuminate the pupil of the objective lens 7 at different positions as shown in FIG. 14. Moreover, by combining with the idea using the polarization beam splitter, it is possible to reduce the number of laser sources to ½ the original number, and thus the cost is also reduced.

Although we have described so far a plurality of ideas, or methods of reducing the laser coherence, illuminating the pupil at a plurality of points and converting the illumination light rays through the objective lens to form the image, these methods can be combined or the equivalents to those methods may be used to reduce the coherence.

Moreover, when a vibrating (or trembling) mirror or the like is placed in part of the light path so that part of the illumination light is changed in its path for laser illumination and when the images formed by light rays passed through different light paths are accumulated on a time basis so that the image can be detected, the time coherence reduction action can be made in that process, and hence it is not necessary to reduce the spatial coherence so strictly as mentioned above.

Figure 22:
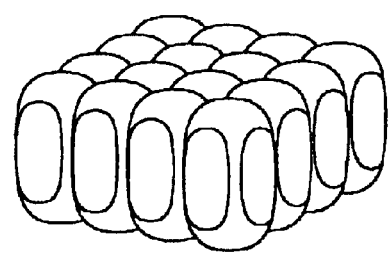
FIG. 22 is a perspective view of a group of glass rod lenses according to the invention.
Figure 23:
FIG. 23 is a perspective view of a multi-cylindrical-lens array according to the invention.

Specifically, when a plurality of spots are formed on the pupil plane, it is not necessary to provide a light path difference beyond the coherence length. As, for example, shown in FIG. 22, a group of glass rod lens (fly eye lens) having uniform length may be used to generate a plurality of light sources from a single laser source. Moreover, a multi-cylindrical lens array that is simpler in its structure than the glass rod lens group may be used as shown in FIG. 23. Since the multi-cylindrical lens array generates a plurality of light sources only in one direction, a plurality of light sources can be two-dimensionally generated by use of two those arrays placed perpendicularly to each other. In that case, by changing the cylinder pitch of each array, it is possible to generate a group of light sources of which the lateral- and longitudinal-array ones respectively have different pitches.

The additional advantage of this method is that, as for example shown in FIG. 26A, when a light source group 252 with its magnification changed is formed on a pupil plane 251 and rotated to scan in a ring-like shape as for example indicated by arrow 254 in FIG. 26A, an on-pupil illumination distribution 253 can be obtained as shaded in FIG. 26B, leading to the ring-band illumination by which the detected image resolution can be improved. In addition, only by changing the magnifying power of the light source group, it is possible to change the ring-band illumination condition. All the pupil plane can be illuminated in order to satisfy σ=1.

Use of the N-stage TDI image sensor of which the scan rate is 1 kHz further adds an advantage. The fundamental period of the galvano mirror may be 1 kHz/N, with which all the pupil plane can be scanned. The galvano mirror of a few kHz is available, and the combination of this mirror and the TDI image sensor will make it possible to scan the pupil at a practical speed, leading to fast image detection. Here, the number of stages in the TDI image sensor (the number of stages) is selected according to the speed of the galvano mirror. Also, by using a stage-variable TDI image sensor, it is possible to change the accumulation time according to the pupil scanning method.

Figure 24:
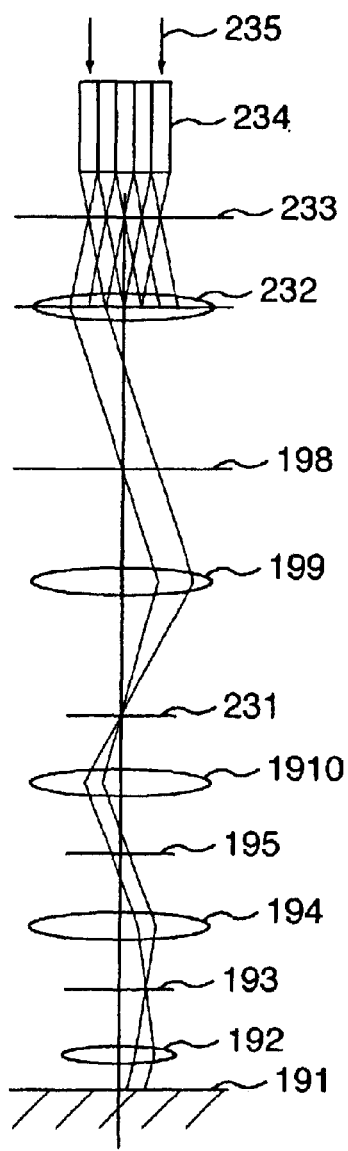
FIG. 24 is a substantially front view of an embodiment of the optical system according to the invention.

FIG. 24 is a diagram showing an illumination system using the above lens array. Although the construction should be shown in a three-dimensional manner as shown in FIG. 21, it is schematically shown here for the purpose of explaining about the important convergence of light. A parallel light flux 235 from a laser source is made incident to a lens array 234 so that a plurality of spots (new light sources) are formed on a second conjugate plane 233 that is conjugated with the pupil plane 193 of the objective lens 192. Then, a plurality of light flux exit, but for the sake of better understanding, a single light flux is shown in FIG. 24. The light rays exiting from the light source group are converted to substantially parallel light flux by a second projection lens 232, and projected on the second scanning mirror surface 198.

The light reflected from the second scanning mirror surface 198 is passed through a first pupil conjugate plane 231 by the second condenser 199, and it is converted to substantially parallel light and projected on a first scanning mirror surface 195 by the first projection lens 1910. Then, the light is converged on the pupil plane 193 by the first condenser 194, and converted to substantially parallel light and irradiated on the sample surface 191 by the objective lens 192. The advantage of this method is that since the plurality of formed spots have outputs corresponding to the intensity distribution of the incident Gaussian beam 235, those spots are superimposed on each other on the sample surface 191 to act as illumination with less illumination intensity distribution.

A description will be made of a method for improving the contrast of the pattern in addition to the increase of the resolution by use of short wavelength.

Figure 25:
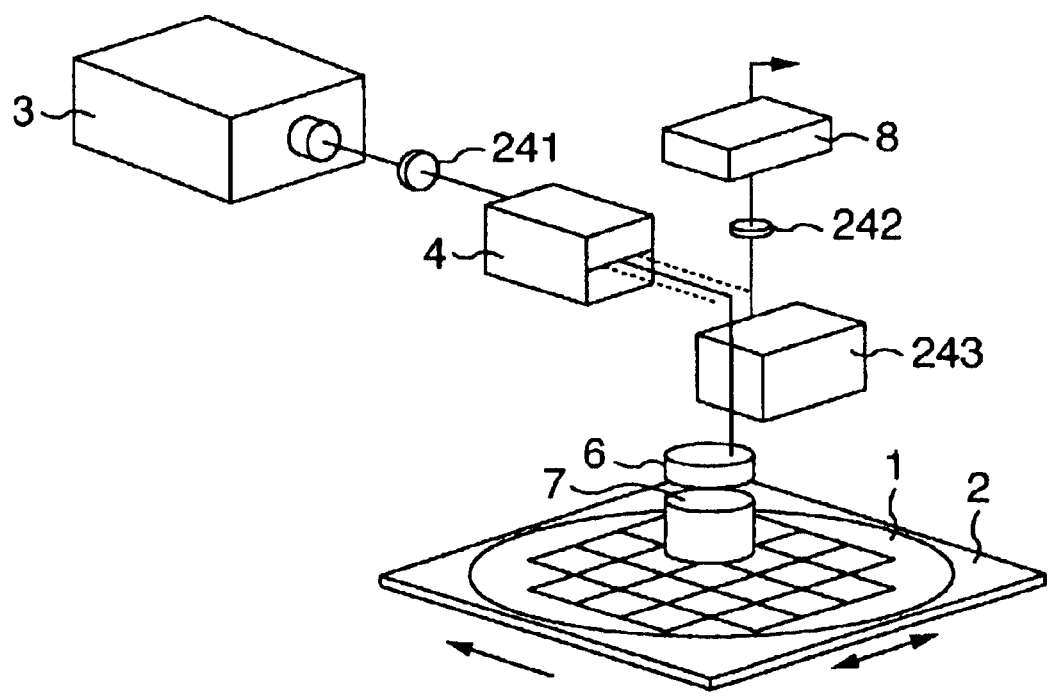
FIG. 25 is a front view of an embodiment of the optical system having a mechanism for controlling the polarized state of the laser illumination according to the invention.

We considered that the polarized state of laser can be freely controlled, and made it possible to detect the polarized component as part of the detected light by controlling the polarization direction and ellipticity of the illumination light in order to improve the pattern contrast. FIG. 25 shows an improved one of the illumination optical system of FIG. 1.

One of the features of laser illumination is linear polarization. When a dichroic mirror is used in the laser beam synthesizer 10, the laser beam can be polarized in the same direction. Thus, the polarized state can be efficiently controlled by a polarizer 241 such as ½ wave plate and ¼ wave plate provided in the light path. For example, the polarized state can be controlled by rotating the ½ wave plate and ¼ wave plate around the optical axis.

Since the pattern contrast is greatly changed by the change of the polarized state of illumination, the performance of the optical system can be improved by making the polarized state controllable (positioning the wave plate by rotation). More specifically, the linear polarization direction can be controlled by the ½ wave plate, and the ellipticity can be changed by the ¼ wave plate. In addition, a desired polarized component can be extracted by an analyzer 242 provided on the detection side. The component that does not contribute to defect detection, for example, 0-order light, can be more reduced, and the component that includes pattern edges such as diffracted light and that contributes to defect detection can be much extracted. Thus, the detection sensitivity can be increased.

The analyzer should be made rotatable in association with the polarized state. By combining these methods, it is also possible to achieve parallel nicols and crossed nicols. Of course, circularly polarized state can be obtained. These states do not depend upon the illumination wavelength itself. If the above concept comes into existence, the actual construction may be arbitrary.

When a polarized beam splitter is used for the laser beam synthesizer 10, the laser beam is, for example, polarized substantially in the perpendicular direction. Thus, the perpendicularly linearly polarized beams are controlled in their polarized states by the polarizer 241 of ½ wave plate and ¼ wave plate.

When the diffracted light from the pattern is observed on the pupil plane of the objective lens (though not shown in FIG. 25, a pupil-observing system is easily provided), more reduction of 0-order light than high-order diffracted light can be confirmed by selecting a polarized state. Thus, it is possible to attenuate the low-frequency component and thus improve the pattern contrast. Of course, a spatial filter may be provided at a position conjugated with the pupil of the objective lens so that the 0-order light can be reduced (the spatial filter can block the diffracted light from the pattern and lead the scattered light from a foreign object to the image sensor). However, by controlling the polarization, it is possible to efficiently extract the high-order diffracted light. The experiment by the inventors shows that the contrast can be improved about 20~300%.

Moreover, the polarizer 241 can be provided at a position where a desired performance can be obtained (for example, between half prism 241 and ¼ wave plate 6) irrespective of the position shown in FIG. 25.

FIG. 27 shows the structure of the image sensor 8 used in FIG. 1. When a DUV laser source is used, it is necessary to use an image sensor that has enough sensitivity to the DUV. The surface irradiation type image sensor cannot effectively detect the DUV light because the incident light is passed through a gate and fed to CCD with the result that the short wavelength incident light is so attenuated that the sensitivity to the wavelength of less than 400 nm is very low. In order to increase the sensitivity of the surface irradiation type image sensor to DUV, it is necessary to use a method of decreasing the thickness of the gate so that the short wavelength light can be prevented from being attenuated.

Alternatively, if cover glass is coated with an organic thin film so that visible light can be emitted therefrom according to the incident DUV light, the image sensor having the sensitivity only to visible light can be used to detect DUV light.

Moreover, since the rear-side irradiation type image sensor is constructed so that the rear side free from gate structure can receive incident light, it has a high quantum efficiency (for example, 30% or above), a wide dynamic range (for example, 3000 or above), and a high sensitivity to wavelengths of 400 nm or below. Thus, it can be profitably used particularly for illumination by wavelengths shorter than 200 nm. This image sensor may be single even when some wavelengths are used.

In addition, use of TDI (Time Delay Integration) type image sensor can raise the sensitivity to light. If the sensor is designed to have antiblooming characteristic, it can solve the problem that when the detected amount of light is more than necessary, the charges are overflowed into the surrounding pixels. Moreover, use of MOS type image sensor and a built-in log amplifier is effective for high dynamic range, and multi-tap construction is also effective for on-chip switching of the stages.

Figure 28:
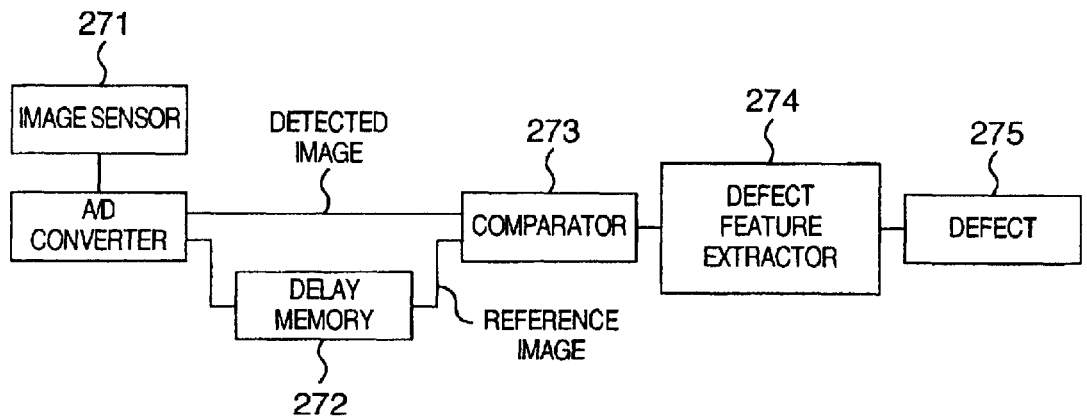
FIG. 28 is a block diagram of the construction for comparing images according to the invention.

FIG. 28 is a block diagram of an example of the processing system for detecting defects from the image fed from the image sensor. Since the object to be inspected has repetitive patterns, prospective points for defects are extracted by comparing the pattern being inspected, with the neighboring pattern. The output signal from the image sensor, 271 is converted from analog to digital signal. A delay memory 272 delays the signal from the A/D converter by the amount corresponding to one pitch in order to produce the reference image for use in the comparison. Thus, the output from the delay memory is the image corresponding to one-pitch delay of the examined image. A comparator 273 compares those two images to produce the difference between the associated pixel values. The resulting image difference is converted to a binary value on the basis of a threshold for defect detection, thus the defect prospective point being extracted.

The threshold for binary conversion is previously determined or determined from the brightness or the like of the image being examined, and all the image is converted to a binary value by use of this threshold.

It can be considered to calculate the threshold at each coordinates of the image or at each brightness, and convert each point of the image to a binary value by use of a different threshold.

Although the image after the binary conversion includes false information, features are extracted from the detected prospective points in order that only defects can be extracted as exactly as possible. A feature value extractor 274 calculates the area, coordinates and projection length of the defect prospective points. Then, decision is made of whether the defect prospective points are actually defects or false information from the calculated feature values, thus finally defect 275 being detected.

Another embodiment including an image processing operation for two images to be compared will be described below. In this embodiment, particularly, the brightness correction is positively performed in order for the two images having different brightness to be compared.

Figure 29:
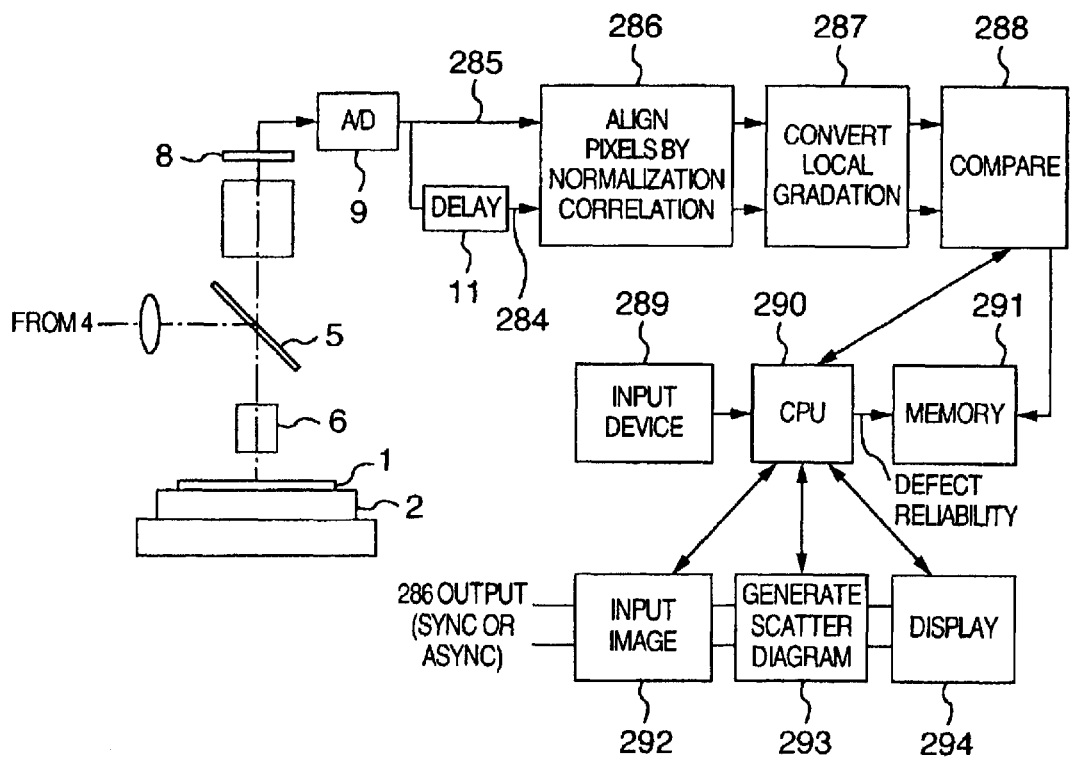
FIG. 29 is a substantially front view showing the construction for determining defects according to the invention.

Referring to FIG. 29, there is shown the image sensor 8 (sensitive to DUV) that generates a shading image signal according to the brightness of the reflected light, or thickness thereof from the semiconductor wafer 1 as the pattern to be examined. Shown at 9 the A/D converter by which the shading image signal produced from the image sensor 8 is converted to a digital image signal 285. The digital image signal is delayed by the delay memory 11. There are shown the stage 2 on which the semiconductor wafer 1 as the pattern being examined is placed and moved together in the X-, Y-, Z- and θ-direction (rotation angle), the objective lens 6 facing the semiconductor waver 1, and the half mirror 5 that reflects the illumination light into the objective lens 6 and then the semiconductor wafer 1, and allows the reflected light from the semiconductor wafer 1 to transmit therethrough. Thus, the illumination light from the laser source is reflected from the half mirror 5 into the object lens 6 and then the semiconductor wafer 1 so that, for example, brightfield illumination is applied on the wafer 1. The pupil of the objective lens 6 is scanned according to the method mentioned previously.

The delay memory 11 may be a memory for storing each cell or each plurality of cell pitches of the image signal 285, thereby delaying, or may be a memory for storing each chip or each plurality chip pitches of the image signal 285.

The digital image signal 285 and delayed digital image signal 284 are aligned with each other by an element block 286. Here, a positional deviation at which the brightness difference between associated pixels becomes the minimum is detected according to normalization correlation, and one of the images is shifted on the basis of this positional deviation so that the two images can be aligned. The normalization is made to reduce the effect of the brightness difference between the images.

That is, a stored image g (x, y) is moved relative to a detected image f (x, y), and a position (Δx, Δy) at which the correlation value R (Δx, Δy) becomes the maximum is calculated from the following equations (Δx, Δy: integer).

$$R(\Delta x, \Delta y) = \sum_{x=0}^{X-1} \sum_{y=0}^{Y-1} \frac{\{f(x, y) - \overline{f}\}\{g(x + \Delta x, y + \Delta y) - \overline{g}(\Delta x, \Delta y)\}}{\sqrt{f_\sigma \cdot g_\sigma(\Delta x, \Delta y)}} \quad (1)$$

$$\overline{f} = \frac{1}{XY} \sum_{x=0}^{X-1} \sum_{y=0}^{Y-1} f(x, y) \quad (2)$$

$$\overline{g}(\Delta x, \Delta y) = \frac{1}{XY} \sum_{x=0}^{X-1} \sum_{y=0}^{Y-1} g(x + \Delta x, y + \Delta y) \quad (3)$$

$$f_\sigma = \sum_{x=9}^{X-1} \sum_{y=0}^{Y-1} \{f(x, y) - \overline{f}\}^2 \quad (4)$$

$$g_\sigma(\Delta x, \Delta y) = \sum_{x=0}^{X-1} \sum_{y=0}^{Y-1} \{g(x + \Delta x, y + \Delta y) - \overline{g}(\Delta x, \Delta y)\}^2 \quad (5)$$

Here, the image is continuously detected by the image sensor, and the image is divided into small regions each of which undergoes alignment. In the above equations, the detected image has a size of X×Y pixels. The division into small regions is made in order to cope with the distortion that the image has. In other words, the small regions are determined in their size so that the image distortion within each small region can be almost neglected.

Although not shown, the above-mentioned normalization correlation for determining the positional deviation of the image is not necessary to make for all image, but for example, may be made for an information-containing one of small image sections (the size of which is X/K×Y pixels) into which the image is divided in the longitudinal direction of the image sensor. The decision of whether information contains in a small image section or not is made by, for example, differentiating each small image section, detecting the presence or absence of an edge and selecting a small image section having more edges. If the image sensor is a linear image sensor of the multi-tap structure capable of parallel outputs, each tap output image corresponds to the small image section. This idea is based on the fact that the parallel output images have an equal positional deviation. In addition, the normalization correlation is separately calculated for each small image section, the maximum positional deviation of the calculated ones for small regions may be employed. The image sensor used here may be the time delay integration TDI CCD of parallel output type that is sensitive to DUV.

The image signals of different brightness are converted in their gradations so that both the brightness values can be equal by use of a gradation converter 287. Here, each pixel is linearly converted by adjusting gain and offset so that both the brightness values can be equal.

The produced image signals are compared with each other by a comparator 288. If there is a disagreement as a result of comparison, it is detected as a defect.

Each pixel of the detected image signal is converted in its gradation on the basis of the above method, and then sequentially undergoes pipe line type image processing. Finally, the defect and its feature are produced.

The operation of the inspection apparatus of the above structure will be described.

Referring to FIG. 29, the illumination light focused by the objective lens 6 scans the semiconductor wafer 1 as the pattern to be examined while the stage 2 is being moved in the X-direction at an equal speed together with the wafer. The image sensor 8 detects the brightness information (brightness image signal) of the pattern formed on the wafer 1, or of the memory mat within a chip and peripheral circuits.

After the movement for one line, the stage is fast moved to the next line in the Y-direction, and positioned. That is, constant speed movement and fast movement are repeated for inspection scanning. Of course, step & repeat type inspection is permissible. The A/D converter 9 converts the output (brightness image signal) of the image sensor 8 to the digital image signal 285. This digital image signal is of 10 bits. Of course, about 6 bits will cause particularly no problem with the image processing. However, in order to detect a very small defect, it is necessary to provide a certain number of bits.

Here, the detection and processing of the image are performed for each pixel at 50 MHz or below. Thus, when wafer disks of 200 mm in diameter are processed, defects including a size of 50 nm or below can be detected at a speed corresponding to a throughput of three disks per hour. Therefore, useful test information in the semiconductor manufacturing line can be produced in a reasonable time.

Thus, according to the invention, it is possible to obtain high-brightness illumination, image high-resolution patterns in a short time, and as a result, produce a high-speed, high-sensitivity inspection apparatus. The information of the detected pattern defects are produced as their positions and sizes.

Moreover, according to the invention, a laser source advantageous for its practical application is used to provide short wavelengths illumination essential for high resolution. The images having a high quality equivalent to or higher than the general discharge tube illumination can be produced with high sensitivity and high speed. Thus, defects can be detected with high sensitivity.

The invention may be embodied in other specific forms without departing from the spirit or essential characteristics thereof. The present embodiments are therefore to be considered in all respects as illustrative and not restrictive. The scope of the invention being indicated by the appended claims rather than by the foregoing description and all changes which come within the meaning and range of equivalency of the claims are therefore intended to be embraced therein.

What is claimed is:

1. A method of inspecting a pattern formed on a substrate, comprising the steps of:
   emitting an ultraviolet laser beam from a light source;
   polarizing the ultraviolet laser beam;
   reducing coherency of the polarized ultraviolet laser beam;
   scanning the polarized and coherence-reduced ultraviolet laser beam on a pupil of an objective lens;
   illuminating a sample with the polarized and coherence-reduced ultraviolet laser beam after the polarized and coherence-reduced ultraviolet laser beam has passed through the objective lens;
   analyzing light reflected from the sample as a result of the illuminating step after the reflected light has passed through the objective lens;
   detecting an image of the sample formed by the analyzed light with a time delay integration sensor;
   outputting signals corresponding to the detected image of the sample from the time delay integration sensor in parallel; and
   processing the parallel signals outputted from the time delay integration sensor to detect a defect of a pattern on the sample.

2. A method of inspecting a pattern according to claim 1, further comprising the step of moving the sample in at least one direction while detecting the image of the sample;
   wherein the detecting step includes the step of detecting the image of the sample with the time delay integration sensor in synchronism with the movement of the sample.

3. A method of inspecting a pattern according to claim 1, wherein the scanning step includes the step of scanning the polarized ultraviolet laser beam annularly on the pupil of the objective lens.

4. A method of inspecting a pattern according to claim 1, wherein the processing step includes the step of detecting a defect less than 50 nm in size.

5. A method of inspecting a pattern formed on a substrate, comprising the steps of:
   emitting an ultraviolet laser beam from a light source;
   reducing coherence of the ultraviolet laser beam;
   scanning the coherence-reduced ultraviolet laser beam annularly on a pupil of an objective lens;
   moving a sample in at least one direction;
   illuminating the moving sample with the coherence-reduced ultraviolet laser beam after the coherence-reduced ultraviolet laser beam has passed through the objective lens;
   detecting an image of the sample formed by light reflected from the sample as a result of the illuminating step with a time delay integration sensor in synchronism with the movement of the sample; and
   processing the detected image of the sample to detect a defect of a pattern on the sample.

6. A method of inspecting a pattern according to claim 5, further comprising the step of polarizing the ultraviolet laser beam before the illuminating step.

7. A method of inspecting a pattern according to claim 5, wherein the detecting step includes the step of controlling a polarization state of the image of the sample.

8. A method of inspecting a pattern according to claim 5, wherein the time delay integration sensor outputs signals corresponding to the detected image of the sample in parallel.

9. A method of inspecting a pattern according to claim 5, wherein the processing step includes the step of converting a local gradation of the detected image of the sample before detecting the defect.

10. A method of inspecting a pattern according to claim 5, wherein the processing step includes the step of detecting a defect less than 50 nm in size.

11. A method of inspecting a pattern according to claim 5, wherein the time delay integration sensor outputs signals corresponding to the detected image of the sample in parallel.

12. A method of inspecting a pattern formed on a substrate, comprising the steps of:
   moving a sample in at least one direction;
   illuminating the sample moving in the at least one direction with an annular-shaped coherence-reduced ultraviolet laser beam which has passed through an objective lens;
   detecting an image of the sample illuminated by the annular-shaped coherence-reduced ultraviolet laser beam with a time delay integration sensor in synchronism with the movement of the sample; and
   processing the detected image of the sample to detect a defect of a pattern on the sample.

13. A method of inspecting a pattern according to claim 12, wherein the illuminating step includes the step of scanning a coherence-reduced ultraviolet laser beam annularly on a pupil of the objective lens to form the annular-shaped coherence-reduced ultraviolet laser beam which has passed through the objective lens.

14. A method of inspecting a pattern according to claim 12, further comprising the step of polarizing the annular-shaped coherence-reduced ultraviolet laser beam before the illuminating step.

15. A method of inspecting a pattern according to claim 12, wherein the detecting step includes the step of controlling a polarization state of the image of the sample.

16. A method of inspecting a pattern according to claim 12, wherein the image of the sample detected in the detecting step is formed on the time delay integration sensor by light reflected from the sample as a result of the illuminating step after the reflected light has passed through a special filter.

17. An apparatus for inspecting a pattern formed on a substrate, comprising:

a light source which emits an ultraviolet laser beam;

a polarizer which polarizes the ultraviolet laser beam;

a coherence reducer which reduces coherency of the polarized ultraviolet laser beam;

a scanner which scans the polarized and coherence-reduced ultraviolet laser beam;

an objective lens through which the polarized and coherence-reduced ultraviolet laser beam scanned by the scanner passes to illuminate a sample;

an analyzer which controls a polarization state of light reflected from the sample as a result of the illumination of the sample after the reflected light has passed through the objective lens;

a time delay integration sensor which detects an image of the sample formed by the reflected light after the reflected light has passed through the analyzer; and a processor which processes a signal outputted from the time delay integration sensor to detect a defect of a pattern on the sample.

18. An apparatus for inspecting a pattern according to claim 17, further comprising:

a table which supports the sample and moves in at least one direction; and a position sensor which detects a position of the table.

19. An apparatus for inspecting a pattern according to claim 17, wherein the scanner scans the polarized ultraviolet laser beam annularly on a pupil of the objective lens.

20. An apparatus for inspecting a pattern according to claim 17, wherein the time delay integration image sensor is a rear-side illumination type time delay integration image sensor.

21. An apparatus for inspecting a pattern according to claim 17, wherein the polarizer includes a ¼ wave plate.

22. An apparatus for inspecting a pattern according to claim 17, wherein the analyzer includes a ¼ wave plate.

* * * * *